United States Patent [19]

Bey et al.

[11] 4,388,466

[45] Jun. 14, 1983

[54] α-HALOMETHYL DERIVATIVES OF AMINO ACIDS

[75] Inventors: Philippe Bey, Strasbourg; Michel Jung, Illkirch Graffestaden, both of France

[73] Assignee: Merrell Toraude et Compagnie, Strasbourg, France

[21] Appl. No.: 317,821

[22] Filed: Nov. 3, 1981

Related U.S. Application Data

[62] Division of Ser. No. 819,975, Jul. 28, 1977, Pat. No. 4,315,095.

[51] Int. Cl.$^3$ .......................................... C07D 233/64

[52] U.S. Cl. .................................... 548/337; 548/344

[58] Field of Search ................................ 548/337, 344

[56] References Cited

U.S. PATENT DOCUMENTS 3,387,031 6/1968 Johnson et al. .................... 548/344

*Primary Examiner*—Richard Raymond

*Attorney, Agent, or Firm*—Raymond A. McDonald; Gary D. Street; William J. Stein

[57] ABSTRACT

Novel halomethyl derivatives of amino acids of the following general structure

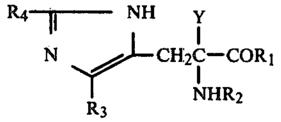

wherein Y is $FCH_2$—, $F_2CH_2$—, $F_3C$—, $ClCH_2$— or $Cl_2CH$—; $R_1$ is hydroxy, a straight or branched alkoxy group of from 1 to 8 carbon atoms, —$NR_{11}R_{12}$ wherein each of $R_{11}$ and $R_{12}$ is hydrogen or a straight or branched lower alkyl group of from 1 to 4 carbon atoms,

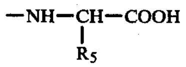

wherein $R_5$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

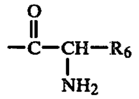

wherein $R_6$ is hydrogen, a straight or branched lower alkyl group of from 1 to 4 carbon atoms, benzyl or p-hydroxybenzyl; each of $R_3$ and $R_4$ is hydrogen, halogen selected from fluorine, chlorine, bromine and iodine, or a straight or branched lower alkyl of from 1 to 4 carbon atoms and may be the same or different with the proviso that when both $R_3$ and $R_4$ are halogen $R_3$ and $R_4$ are the same; and pharmaceutically acceptable salts thereof.

5 Claims, No Drawings

α-HALOMETHYL DERIVATIVES OF AMINO ACIDS

This is a division, of application Ser. No. 819,975, filed July 28, 1977 now U.S. Pat. No. 4,315,095.

FIELD OF INVENTION

This invention relates to novel pharmaceutically useful halomethyl derivatives of histidine and related compounds.

BACKGROUND OF INVENTION

Most mammalian tissue contains histamine, concentration being particularly high in the skin, intestinal mucosa and the lungs. Every mammalian tissue that contains histamine, including white blood cells, appears capable of synthesizing the amine from histidine. The principal enzyme involved in catalyzing in vivo the conversion of histidine to histamine is histidine decarboxylase which is specific for the substrate L-histidine. In many tissues the chief storage site of histamine is the mast cell, or in the case of blood, the basophil which is the circulating counterpart of the fixed-tissue mast cell. Mast cells are not the only tissue source of histamine which is present in substantial amounts in the human epidermis, the central nervous system and the gastrointestinal mucosa.

Histamine is involved in various physiological processes. Histamine is released during the antigen-antibody reaction and is responsible, in large part, for the hypersensitivity reaction characterized by vasodilation, itching and edema formation. This type of antigen-antibody reaction wherein the principal cells involved are mast cells and basophils from which histamine is released is commonly referred to as an immediate hypersensitivity reaction. In addition to antigens, or allergens, histamine is released by many chemical substances, macromolecules, venoms, physical insult, such as heat and other injurious stimuli. Gastric acid secretion is known to be stimulated by histamine. Also, histamine is known to be frequently involved in initiation of sensory impulses evoking pain and itching. It has also been found that histamine levels are high in many tissues undergoing rapid growth, for example, embryonic tissue, regenerating liver and malignant growths.

Correlations between levels of histamine and histidine decarboxylase activity in tissues have been made. In the brain which contains histamine and histidine decarboxylase the turnover of histamine is rapid being augmented by stressful stimuli that also increases histidine decarboxylase activity. Inhibitors of L-histidine decarboxylase, such as, α-hydrazinohistidine are known to lower histamine concentrations. In rat fetal tissue, wherein high levels of histamine are present, it has been shown that inhibition of L-histidine decarboxylase arrests fetal development.

The effects of histamine and its mode of action are well documented. It is believed that the amine exerts its effect through at least two receptors being classified as $H_1$ and $H_2$ receptors. Several agents are known to counter the effects of histamine, however, not all such agents prevent the formation of histamine. For example, classical antihistamines useful in treating allergic reactions are believed to exert their utility by interfering with the binding of histamine with $H_1$ receptors. Similarly agents useful in countering the stimulant effect of histamine on gastric acid secretion are believed to operate by interfering with the binding of histamine with $H_2$ receptors.

Agents capable of blocking $H_1$ receptors find use in treating acute exudative types of allergy, such as, seasonal rhinitis, hay fever, pollinosis relieving the sneezing, rhinorrhea, itching eyes, nose and throat. Such agents are also useful in controlling cough and to a degree find use in treating systemic anaphylaxis and bronchial asthma. Antihistamine agents which act through $H_1$ receptors are also useful in treating allergic dermatoses, such as acute and chronic urticaria, angioedema, itching pruritides, for example, atopic dermatitis and contact dermatitis, in the control of urticarial and edematous lesions of serum sickness, control of blood transfusion reactions and control of drug reactions attributable to allergic phenomena. Agents which block $H_2$ receptors are useful in treating peptic ulceration, the Zollinger-Ellison syndrome and other gastric hypersecretory states.

Agents which block the formation of histamine by inhibiting the activity of histidine decarboxylase, for example, α-methylhistidine and α-hydrazinohistidine, are reported to be useful in the same manner as antihistaminic agents that are blockers of $H_1$ and $H_2$ receptors. Additionally histidine decarboxylase inhibitors are implicated as being useful in the control of certain tumors which are high in histamine content.

The compounds of the present invention prevent the formation of histamine by inhibiting the action of histidine decarboxylase rendering said compounds useful in treating pathophysiological conditions which result from histamine. The presently claimed compounds can be used in the same manner and for the same purposes as are compounds that antagonize $H_1$ and $H_2$ receptors.

SUMMARY OF INVENTION

The compounds of the present invention are represented by the following general Formula I:

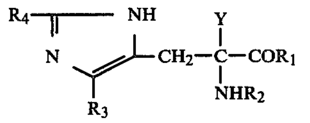

Formula I

In the above general Formula I Y is $FCH_2$—, $F_2CH$—, $F_3C$—, $ClCH_2$— or $Cl_2CH$—; each of $R_3$ and $R_4$ is hydrogen, halogen selected from fluorine, chlorine, bromine and iodine or a straight or branched lower alkyl group of from 1 to 4 carbon atoms and can be the same or different with the proviso that when both $R_3$ and $R_4$ are halogen $R_3$ and $R_4$ are the same; $R_1$ is hydroxy, a straight or branched lower alkoxy group of from 1 to 8 carbon atoms, —$NR_{11}R_{12}$ wherein each of $R_{11}$ and $R_{12}$ is hydrogen or a straight or branched lower alkyl group of from 1 to 4 carbon atoms, or

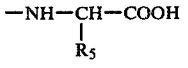

wherein $R_5$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

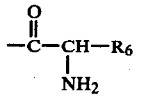

wherein $R_6$ is hydrogen, a straight or branched lower alkyl group of from 1 to 4 carbon atoms, benzyl or p-hydroxybenzyl.

The pharmaceutically acceptable salts and individual optical isomers of the compounds of general Formula I are also included within the scope of this invention.

DETAILED DESCRIPTION OF INVENTION

Illustrative examples of straight or branched alkoxy groups of from 1 to 8 carbon atoms in the above general Formula I are methoxy, ethoxy, n-propoxy, n-butoxy, isopropoxy, tert-butoxy, pentoxy, and octyloxy.

Illustrative examples of straight chain or branched chain lower alkyl groups of from 1 to 4 carbon atoms in the above general Formula I are methyl, ethyl, n-propyl, isopropyl, n-butyl and tert-butyl.

As used in general Formula I the term alkylcarbonyl is taken to mean the group

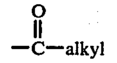

wherein the alkyl group is straight or branched and has from 1 to 4 carbon atoms, for example, methyl, ethyl, n-propyl, isopropyl, n-butyl and tert-butyl.

As used in general Formula I the term alkoxycarbonyl is taken to mean the group

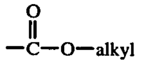

wherein the alkoxy group, that is, —O-alkyl has from 1 to 4 carbon atoms and is straight or branched, for example, methoxy, ethoxy, n-propoxy, isopropoxy, n-butoxy and tert-butoxy.

Illustrative examples of pharmaceutically acceptable salts of the compounds of this invention include nontoxic acid addition salts formed with inorganic acids, such as, hydrochloric, hydrobromic, sulfuric and phosphoric acid, and organic acids, such as, methane sulfonic, salicylic, maleic, cyclamic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Compounds of general Formula I wherein $R_2$ is hydrogen or alkylcarbonyl as defined above, $R_1$ is hydroxy or a straight or branched alkoxy group of from 1 to 8 carbon atoms are preferred. More preferred compounds of this invention are those of general Formula I wherein $R_1$ is hydroxy or a straight or branched alkoxy group of from 1 to 8 carbon atoms, $R_2$ is hydrogen and each of $R_3$ and $R_4$ is hydrogen, chlorine, fluorine or methyl. Compounds wherein Y is $FCH_2$—, $F_2CH$— or $ClCH_2$— are also preferred.

Illustrative examples of compounds of the present invention are the following:

2-amino-2-difluoromethyl-3-(5-imidazolyl)propionic acid,
2-amino-2-fluoromethyl-3-[5-(4-fluoro)imidazolyl]propionic acid,
2-amino-2-chloromethyl-3-[5-(2-fluoro)imidazolyl]propionic acid,
2-amino-2-dichloromethyl-3-[5-(4-methyl)imidazolyl]propionic acid,
2-amino-2-trifluoromethyl-3-[5-(2-methyl)imidazolyl]propionic acid,
2-amino-2-fluoromethyl-3-[5-(4-ethyl)imidazolyl]propionic acid,
2-amino-2-difluoromethyl-3-[5-(2-ethyl)imidazolyl]propionic acid,
2-amino-2-dichloromethyl-3-[5-(4-n-propyl)imidazolyl]propionic acid,
2-amino-2-chloromethyl-3-[5-(2-n-propyl)imidazolyl]propionic acid,
2-amino-2-dichloromethyl-3-[5-(4-isopropyl)imidazolyl]propionic acid,
2-amino-2-trifluoromethyl-3-[5-(2-isopropyl)imidazolyl]propionic acid,
2-amino-2-dichloromethyl-3-[5-(4-n-butyl)imidazolyl]propionic acid,
2-amino-2-fluoromethyl-3-[5-(2-n-butyl)imidazolyl]propionic acid,
2-amino-2-difluoromethyl-3-[5-(4-tert-butyl)imidazolyl]propionic acid,
2-amino-2-dichloromethyl-3-[5-(2-tert-butyl)imidazolyl]propionic acid,
2-amino-2-fluoromethyl-3-[5-(2,4-difluoro)imidazolyl]propionic acid,
2-amino-2-trifluoromethyl-3-[5-(2,4-dimethyl)imidazolyl]propionic acid,
2-amino-2-difluoromethyl-3-[5-(2,4-diethyl)imidazolyl]propionic acid,
2-amino-2-difluoromethyl-3-(5-(2,4-di-n-propyl)imidazolyl]propionic acid,
2-amino-2-fluoromethyl-3-[5-(2,4-diisopropyl)imidazolyl]propionic acid,
2-amino-2-fluoromethyl-3-[5-(2,4-di-n-butyl)imidazolyl]propionic acid,
2-amino-2-chloromethyl-3-[5-(2,4-di-tert-butyl)imidazolyl]propionic acid,
methyl 2-amino-2-dichloromethyl-3-(5-imidazolyl)propionate, ethyl 2-amino-2-trifluoromethyl-3-[5-(4-fluoro)imidazolyl]propionate,
n-propyl 2-amino-2-trifluoromethyl-3-[5-(2-fluoro)imidazolyl]propionate,
N-n-butyl 2-amino-2-dichloromethyl-3-[5-(4-methyl)imidazolyl]propionamide,
isopropyl 2-amino-2-chloromethyl-3-[5-(2-methyl)imidazolyl]propionate,
tert-butyl 2-amino-2-fluoromethyl-3-[5-(4-ethyl)imidazolyl]propionate,
n-pentyl 2-amino-2-fluoromethyl-3-[5-(2-ethyl)imidazolyl]propionate,
isopentyl 2-amino-2-chloromethyl-3-[5-(4-n-propyl)imidazolyl]propionate,
tert-pentyl 2-amino-2-dichloromethyl-3-[5-(2-n-propyl)imidazolyl]propionate,
n-hexyl 2-amino-2-difluoromethyl-3-[5-(4-isopropyl)imidazolyl]propionate, n-heptyl 2-amino-2-difluoromethyl-3-[5-(2-isopropyl)imidazolyl]propionate, n-octyl 2-amino-2-fluoromethyl-3-[5-(4-n-butyl)imidazolyl]propionate, methyl 2-amino-2-fluoromethyl-3-[5-(2-n-butyl)imidazolyl]propionate, N,N'-dimethyl 2-amino-2-chloromethyl-3-[5-(4-tert-butyl)imidazolyl]propionamide, N-n-propyl 2-amino-2-trifluoromethyl-3-[5-(2,4-difluoro)imidazolyl]propionamide, N-n-butyl 2-amino-2-difluoromethyl-3-[5-(2,4-dimethyl)imidazolyl]propionamide, ethyl 2-amino-2-fluoromethyl-3-[5-(2,4-diethyl)imidazolyl]propionate, n-butyl 2-amino-2-fluoromethyl-3-[5-(2,4-di-n-propyl)imidazolyl]propionate, N-ethyl 2-amino-2-difluoromethyl-3-[5-imidazolyl]propionamide, N-methyl 2-amino-2-trifluoromethyl-3-[5-(4-n-butyl)imidazolyl]propionamide, N-n-propyl 2-amino-2-chloromethyl-3-[5-(2-fluoro)imidazolyl]propionamide, 2-[2-amino-2-dichloromethyl-3-(5-imidazolyl)-1-oxopropylamino]acetic acid, 2-[2-amino-2-fluoromethyl-3-(5-imidazolyl)-1-oxopropylamino]propionic acid, 2-[2-amino-2-difluoromethyl-3-[5-(2-methyl)imidazolyl]-1-oxopropylamino]-2-benzylacetic acid, 2-[2-difluoromethyl-2-(1-oxoethylamino)-3-(5-(4-fluoro)imidazolyl]-1-oxopropylamino)acetic acid, 2-[2-(N-ethoxycarbonylamino)-2-fluoromethyl-3-[5-(4-methyl)imidazolyl]-1-oxopropylamino]acetic acid, N,N'-diethyl 2-dichloromethyl-2-(1-oxoethylamino)-3-[5-(2-fluoro)imidazolyl]propionamide, 2-chloromethyl-2-(1-oxoethylamino)-3-(5-imidazolyl)-propionic acid, 2-dichloromethyl-2-(N-propoxycarbonylamino)-3-[5-(2-methyl)imidazolyl]propionic acid, ethyl 2-[N-(2-amino-1-oxoethyl)amino]-2-difluoromethyl-3-(5-imidazolyl)propionate, N-methyl 2-[N-(2-amino-1-oxo-3-phenylpropyl)amino]-2-chloromethyl-3-[5-(2-fluoro)imidazolyl]propionamide, 2-amino-2-chloromethyl-3-[5-(4-chloro)imidazolyl]propionic acid, 2-amino-3-[5-(2-chloro)imidazolyl]-2-difluoromethylpropionic acid, 2-amino-3-[5-(2-chloro-4-methyl)imidazolyl]-2-difluoromethylpropionic acid, 2-amino-3-[5-(2-bromo)imidazolyl]-2-trifluoromethylpropionic acid, and 2-amino-2-fluoromethyl-3-[5-(2-iodo)imidazolyl]propionic acid, The compounds of this invention, that is, the compounds of Formula I are irreversible inhibitors of histidine decarboxylase, the enzyme which in vivo converts histidine to histamine. Thus, the compounds block the formation of histamine which is known to play an important role in certain patho-physiological conditions. As inhibitors of histidine decarboxylase the compounds of Formula I are useful in the same manner as any known antihistaminic agent whether such agent exerts its effectiveness by blocking $H_1$ or $H_2$ receptors or other means. The compounds of this invention are useful in treating patho-physiological conditions due to histamine, hence, the compounds have many utilities being useful in treating acute exudative types of allergy, such as, seasonal rhinitis, hay fever, and pollinosis relieving the sneezing, rhinorrhea, itching eyes, nose and throat. The compounds of general Formula I are also useful in controlling cough and in treating systemic anaphylaxis and bronchial asthma, and are useful as bronchodilators. Also, the compounds of this invention are useful in treating allergic dermatoses, such as, acute urticaria, chronic urticaria, angioedema, itching pruritides, for example, atopic dermatitis and contact dermatitis. The compounds of this invention are also useful in treating urticarial and edematous lesions of serum sickness, blood transfusion reactions attributable to allergic phenomena and nausea. The compounds of general Formula I are also useful in treating peptic ulceration, the Zollinger-Ellison syndrome and other gastric hypersecretory states. As described hereinabove it has been found that histamine levels are high in rapidly growing tissues, such as, tumors, hence, the compounds of general Formula I by inhibiting the formation of histamine, may be useful in controlling the growth of certain tumors, for example, Walker mammary carcinoma and Erlich ascitic tumors.

The compounds of Formula I can be administered in various manners to achieve the desired effect. The compounds can be administered alone or in the form of pharmaceutical preparations to the patient being treated either orally, parenterally, that is, subcutaneously, intravenously or intraperitoneally, or topically. The compounds can be administered by intranasal instillation or by application to mucous membranes such as that of the nose, throat and bronchial tubes, for example, in an aerosol spray containing small particles of a novel compounds of this invention in a spray solution or dry powder form.

The amount of novel compound of this invention administered will vary and can be any effective amount. Depending on the patient, the condition being treated and the mode of administration, the quantity of novel compound administered may vary over a wide range to provide as an effective amount in a unit dosage form of from about 0.1 to 500 mg/kg (milligrams per kilogram) of body weight of the patient per dose and preferably from about 50 to 200 mg/kg to achieve the desired effect. For example, the desired effect can be obtained by consumption of a unit dosage form, such as, for example, a tablet containing from 10 to 500 mg of a novel compound of this invention taken 1 to 4 times daily.

As used herein the term patient is taken to mean warm blooded animals such as birds and mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents, such as corn starch, potato starch, or alginic acid, and a lubricant such as stearic acid, or magnesium stearate.

For parenteral administration the compounds of Formula I may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds of Formula I can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds of Formula I in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary or desirable. The compounds may also be administered in a non-pressurized form such as in a nebulizer or atomizer.

The utility of the compounds of general Formula I as irreversible inhibitors of histidine decarboxylase may be demonstrated as follows. A compound of general Formula I is administered as an aqueous solution or suspension to rats or mice either orally or parenterally. At different time intervals after administration of the test compound the animals are injected intraperitoneally with 2 $\mu$Ci of 2-$^{14}$C-L-histidine. Two hours after the labeled histidine injection the animals are sacrificed, and the amount of radio active histamine present in the glandular part of the stomach is determined as described by K. M. Mole and D. M. Shepherd, J. Pharm. Pharmac. 25, 609-613 (1973).

In addition to being useful pharmacological agents, the compounds of Formula I wherein $R_1$ is hydroxy and R is hydrogen are useful as intermediates for the preparation of cephalosporin derivatives of the following general Formula II which are useful as antibiotics.

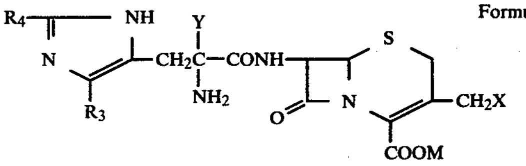

Formula II

In the above general Formula II X is hydrogen or acetoxy; M is hydrogen or a negative charge, and $R_3$, $R_4$ and Y have the meanings defined in general Formula I.

The compounds of general Formula II and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula II are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of cephalosporin derivatives as represented by general Formula II are 7-[[2-amino-2-difluoromethyl-3-(5-imidazolyl)propionyl]amino]-3-acetyloxymethyl-8-oxo-5-thia-1-azabicyclo[4.2.0]oct-2-ene-2-carboxylic acid, 7-[[2-amino-2-fluoromethyl-3-[2-(methyl)-5-imidazolyl]propionyl]amino]-3-acetyloxymethyl-8-oxo-5-thia-1-azabicyclo[4.2.0]oct-2-ene-2-carboxylic acid and 7-[[2-amino-2-difluoromethyl-3-[2-fluoro-5-imidazolyl]propionyl]amino]3-acetyloxy-8-oxo-5-thia-1-azabicyclo[4.2.0]oct-2-ene-2-carboxylic acid.

The preparation of the compounds of general Formula II is described hereinbelow.

The $\alpha$-halomethyl histidine derivatives of this invention wherein $R_1$ is hydroxy, $R_2$ is hydrogen and $R_3$ and $R_4$ have the meanings defined in general Formula I are prepared by treating one equivalent of a suitably protected histidine derivative of the formula

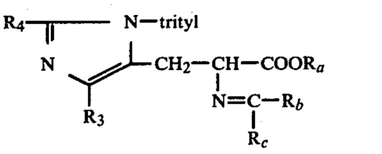

Formula III with one equivalent of a suitable strong base to generate a carbanion intermediate followed by treatment with one equivalent of a suitable halomethylhalo alkylating reagent and subsequently hydrolyzing with acid. In the above general Formula III $R_a$ is a straight or branched alkyl group having from 1 to 8 carbon atoms, $R_b$ is hydrogen, phenyl, a straight or branched alkyl group of from 1 to 8 carbon atoms, methoxy or ethoxy; $R_c$ is phenyl or a straight or branched alkyl group of from 1 to 8 carbon atoms; or $R_b$ and $R_c$ taken together form an alkylene group of from 5 to 7 carbon atoms, that is, $-CH_2-(CH_2)_m-CH_2-$ wherein m is an integer of from 3 to 5. Illustrative examples of straight or branched alkyl groups of from 1 to 8 carbon atoms which $R_b$ and $R_c$ may represent are methyl, ethyl, n-propyl, isopropyl, n-butyl, tert-butyl, n-hexyl, n-octyl, and neopentyl. Each of $R_3$ and $R_4$ has the meaning defined in general Formula I.

Suitable strong bases which may be employed in the above reaction sequence to form the carbanion intermediate are those which will abstract a proton from the carbon atom alpha to the carboxy group such as, alkyl lithium, for example, butyl lithium or phenyl lithium, lithium dialkylamide, for example, lithium diisopropylamide, or lithium amide, tertiary potassium butylate, sodium amide, metal hydrides, for example, sodium hydride or potassium hydride, tertiary amines, such as, triethylamine, lithium acetylide or dilithium acetylide. Lithium acetylide, dilithium acetylide, sodium hydride and lithium diisopropylamide are preferred bases.

Suitable halomethylhalo alkylating reagents which may be employed in the above reaction are illustratively chlorofluoromethane, bromofluoromethane, fluoroiodomethane, chlorodifluoromethane, bromodifluoromethane, difluorodomethane, bromotrifluoromethane, chlorotrifluoromethane, trifluoroidomethane, bromochloromethane, dichloromethane, chloroiodomethane, bromidichloromethane and dichloroiodomethane. The halomethylhalo alkylating reagents are known in the art.

The alkylating reaction may be carried out in an aprotic solvent, for example, benzene, toluene, ethers, tetrahydrofuran, dimethylsulfoxide or hexamethylphosphortriamide. The reaction temperature may vary from about −120° C. to about 65° C., a preferred reaction temperature being about 25° to 55° C. The reaction time will vary from about ½ hour to 24 hours.

Acid hydrolysis to remove any unreacted starting material and protecting groups may be achieved in one step or stepwise. In a one-step hydrolysis procedure the concentration of acid employed will obviously vary with the duration of the hydrolysis step and temperature employed. For example, one-step hydrolysis may be achieved by treatment with concentrated hydrochloric acid for 1 to 4 days at about 25° to 120° C. Stepwise hydrolysis may be achieved by treatment with dilute acid for about ½ hour to 6 hours at about 25° C. to remove unreacted starting material repeating treatment with dilute acid to remove any amine protecting groups followed by treatment with concentrated acid for about 1 to 3 days at about 25° to 125° C. to remove any ester or ether groups. Stepwise hydrolysis is preferred.

The compounds of general Formula III are prepared by treating an appropriately substituted N'-monotritylhistidine lower alkyl ester, such as, the methyl, ethyl or n-propyl ester in a solvent, such as, an ether, for example, diethyl ether or tetrahydrofuran, aromatic hydrocarbons, such as, benzene, methylene chloride or chloroform with a carbonyl bearing compound to form a Schiff's base in a generally known manner, specifically (a) when $R_b$ is hydrogen, by treating the appropriate amino acid ester with benzaldehyde or an alkanol having from 1 to 9 carbon atoms being straight or branched, for example, 1-propanal, 1-butanal, 2,2-dimethylpropan-1-al or 2,2-diethylbutan-1-al, (b) when $R_b$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone, and (c) when $R_b$ is a straight or branched alkyl group having from 1 to 8 carbon atoms, treating the appropriate amino acid ester with a phenyl alkyl ketone as described above with a dialkyl ketone wherein each alkyl moiety has from 1 to 8 carbon atoms and is straight or branched, for example, dimethyl isopropyl ketone, di-n-butyl ketone or methyl tert-butyl ketone. The carbonyl bearing compounds are known in the art or may be prepared by procedures well known in the art.

When $R_b$ is methoxy or ethoxy in compounds of Formula III an appropriate amino acid ester is reacted with benozyl halide, for example, chloride or an alkanoic acid halide, for example, chloride wherein the alkanoic acid has from 1 to 9 carbon atoms and may be straight or branched, such as acetyl chloride, propionyl chloride, butyryl chloride, tert-butyryl chloride, 2,2-diethylbutyric acid chloride or valeryl chloride at 0° C. in ethers, methylenechloride, dimethylformamide, dimethylacetamide, or chlorobenzene in the presence of an organic base such as triethylamine or pyridine after which the reaction mixture is allowed to warm to about 25° C. for 1 hour. The resulting amide derivative is combined with an alkylating reagent, such as, methylfluorosulfonate, dimethylsulfate, methyliodide, methyl, p-toluenesulfonate or trimethyloxonium hexafluorophosphate when $R_b$ is methoxy or triethyloxonium tetrafluoroborate when $R_b$ is ethoxy at about 25° C. in a chlorinated hydrocarbon solvent, such as, methylene chloride, chlorobenzene or chloroform, and the reaction mixture is refluxed for about 12 to 20 hours. The mixture is then cooled to about 25° C. and an organic base, such as, triethylamine or pyridine is added after which the solution is extracted with brine and the product isolated.

When in the compounds of Formula III $R_b$ and $R_c$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

The appropriately substituted N'-monotritylhistidine lower alkyl esters are prepared from the corresponding ester hydrochlorides by treatment with a saturated solution of sodium bicarbonate, and the free base is extracted with chloroform. The tritylester hydrochlorides are prepared from histidine or histidine substituted at the 2 and/or 4-positions with a halogen selected from fluorine, chlorine, bromine or iodine or a lower alkyl group of from 1 to 4 carbon atoms and the 2- and 4-position substituents can be the same or different with the proviso that when both the 2- and 4-position substituents are halogen they are the same by the general methods described by G. C. Stelakatos et al., J. Am. Chem. Soc. 81, 2884 (1959). The 2,4-substituted histidine derivatives are known in the art or can be prepared by procedures generally known in the art, for example, as illustrated in the specific examples contained herein.

The compounds of general Formula I wherein $R_1$ is a straight or branched alkoxy group of from 1 to 8 carbon atoms are prepared from the corresponding derivatives wherein $R_1$ is hydroxy by reaction with an alcohol of the formula $R_7$—OH wherein $R_7$ is a straight or branched alkyl group of from 1 to 8 carbon atoms, such as, methyl, ethyl, n-propyl, isopropyl, n-butyl, tert-butyl, hexyl or octyl, saturated with HCl gas at about 25° C. for from 12 to 36 hours.

The compounds of general Formula I wherein $R_1$ is —$NR_{11}R_{12}$ wherein each of $R_{11}$ and $R_{12}$ is hydrogen or a lower alkyl group of from 1 to 4 carbon atoms are prepared by an acylation reaction of an acid halide, for example, an acid chloride, of the corresponding compound wherein each $R_1$ is hydroxy and $R_2$ has the meaning defined in Formula I with the proviso that any free amino group is suitably protected with, for example, carbobenzyloxy or tert-butoxycarbonyl, and the 2-imidazole nitrogen is protected with carbobenzyloxy or 2,4-dinitrophenyl, with an excess of an appropriate amine which may be represented as $HNR_{11}R_{12}$. The reaction is carried out in methylene chloride, chloroform, dimethylformamide ethers, such as, tetrahydrofuran or dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine or di-n-butylamine. Following the acylation reaction the protecting groups are removed by treatment with acid, for example, trifluoroacetic acid or hydrogen bromide in dioxane followed by treatment with base such as aqueous sodium hydroxide.

The compounds of general Formula I wherein $R_1$ is

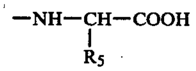

are prepared by reacting the corresponding derivative wherein $R_1$ is hydroxy or a functional derivative thereof such as an acid anhydride and $R_2$ has the meaning defined in Formula I with the proviso that any free amino group is protected with a suitable blocking group, such as benzyloxycarbonyl or tert-butoxycarbonyl and the 1-imidazole nitrogen is protected with benzyloxycarbonyl or 2,4-dinitrophenyl with a compound of the formula

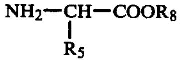

wherein $R_5$ has the meaning defined in general Formula I and $R_8$ is a lower alkyl group, for example, methyl or ethyl in an ether, for example, tetrahydrofuran or dioxane at 0° to 50° C. for about 1 to 24 hours followed by acid and base hydrolysis to remove the protecting groups, with the proviso that when the amine protected free acid is employed the reaction is carried out using a dehydrating agent such as dicyclohexylcarbodiimide.

The compounds of general Formula I wherein $R_2$ is alkylcarbonyl wherein the alkyl moiety is straight or branched and has from 1 to 4 carbon atoms are prepared by treating the corresponding derivative wherein $R_1$ is hydroxy and $R_2$ is hydrogen with an acid halide of the formula

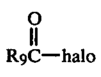

wherein halo is a halogen atom, for example, chlorine or bromine and $R_9$ is a straight or branched alkyl group having from 1 to 4 carbon atoms in water in the presence of a base such as sodium hydroxide or sodium borate at a temperature of from about 0° to 25° C. for from about ½ hour to 6 hours. These compounds may also be prepared from the ester derivative, that is, compounds of general Formula I wherein $R_2$ is hydrogen and $R_1$ is an alkoxy group of from 1 to 8 carbon atoms by treatment with the acid halide,

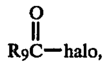

described above, in water, methylene chloride, chloroform or dimethyl acetamide in the presence of a base such as sodium hydroxide, potassium hydroxide or excess triethylamine at a temperature of from 0° to 25° C. for from ½ hour to 24 hours.

The compounds of general Formula I wherein $R_2$ is alkoxycarbonyl wherein the alkoxy moiety is straight or branched and has from 1 to 4 carbon atoms are prepared by treating the corresponding derivative wherein $R_2$ is hydrogen and $R_1$ is hydroxy with a halo alkylformate of the formula

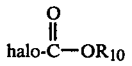

wherein halo is halogen atom such as chlorine or bromine and $R_{10}$ is a straight or branched alkyl group having from 1 to 4 carbon atoms in water in the presence of a base such as sodium hydroxide or sodium borate at a temperature of from about 0° to 25° C. for from about ½ hour to 6 hours.

The compounds of general Formula I wherein $R_2$ is

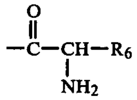

wherein $R_6$ is hydrogen, a straight or branched lower alkyl group of from 1 to 4 carbon atoms, benzyl or p-hydroxybenzyl are prepared by treating the corresponding derivative wherein $R_2$ is hydrogen, $R_1$ is a straight or branched alkoxy group of from 1 to 8 carbon atoms and the 1-imidazole nitrogen is protected with benzyloxycarbonyl or 2,4-dinitrophenyl with an acid of the formula

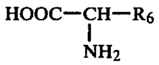

or an anhydride thereof wherein the amino group is protected with a suitable blocking group such as benzyloxycarbonyl or tert-butoxycarbonyl and $R_6$ has the meaning defined hereinabove in an ether, such as, tetrahydrofuran or dioxane, methylene chloride or chloroform, and in the presence of a dehydrating agent such as dicyclohexylcarbodiimide when the free acid is employed, at a temperature of from about 0° C. to 35° C. for about 1 to 12 hours followed by acid and base hydrolysis to remove the protecting groups.

The individual optical isomers of the compounds of Formula I wherein $R_2$ is H and $R_1$ is OH may be separated by using a (+) or (−) binaphthylphosphoric acid salt by the method of R. Viterbo et al., Tetrahedron Letters 48, 4617 (1971). The individual optical isomers of compounds wherein $R_2$ and $R_1$ are other than H and OH respectively are prepared as described herein for the racemic mixture only starting with the resolved amino acid.

As set forth hereinabove the compounds of general Formula I wherein $R_1$ is hydroxy and $R_2$ is hydrogen are useful as intermediates for the preparation of useful cephalosporin derivatives as described by general Formula II. The compounds of general Formula II are prepared by coupling 7-aminocephalosporanic acid or a derivative thereof having the formula

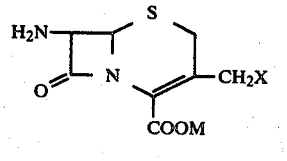

Formula IV wherein X and M have the meaning defined in general Formula II with an acid of the following Formula V or a functional derivative thereof, such as, the acid chloride or an acid anhydride

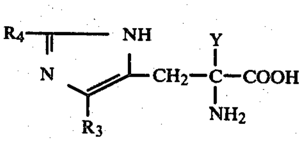

Formula V wherein Y, $R_3$ and $R_4$ have the meanings defined in Formula I and the amino groups are protected by suitable blocking groups, for example, an acid salt, such as hydrochloride salt, an acyl group, or tert-butoxycarbonyl which groups are removed after the coupling reaction by acid hydrolysis.

The coupling reaction is generally carried out in a solvent, such as, ethyl acetate, dioxane, chloroform or tetrahydrofuran in the presence of a base, such as alkaline bicarbonate. The temperature of the reaction may vary from −10° C. to 100° C., and the reaction time may very from about ½ hour to 10 hours. The cephalosporin products are isolated by conventional means.

The following illustrates the use of the compounds of general Formula I wherein $R_1$ is hydroxy in the preparation of the useful cephalosporin derivatives of general Formula II.

EXAMPLE 1

7-[[2-Amino-2-difluoromethyl-3-(5-imidazolyl)propionyl]amino]-3-acetoxymethyl-8-oxo-5-thia-1-azabicyclo[4.2.0]oct-2-ene-2-carboxylic acid A mixture of 1 g of 3-acetyloxymethyl-7-amino-8-oxo-5-thia-1-azabicyclo[4.2.0]oct-2-ene-2-carboxylic acid and 1 g of 2-amino-2-difluoromethyl-3-(5-imidazolyl)propionic acid chloride wherein the free amino groups are protected with tertiary-butoxycarbonyl in 50 ml of ethyl acetate is refluxed for 2 hours after which the solvent is removed leaving a residue which is chromatographed on silica gel using benzene-acetone as the eluant to give 7-[[2-amino-2-difluoromethyl-3-(5-imidazolyl)propionyl]amino]-3-acetoxymethyl-8-oxo-5-thia-1-azabicyclo[4.2.0]oct-2-ene-2-carboxylic acid wherein the amino groups are protected with tert-butoxycarbonyl. The protected cephalosporin compound is treated with trifluoroacetic acid for ½ hour at 25° C. under nitrogen atmosphere then diluted with ether until precipitation stops and filtered to give the di-trifluoroacetic acid salt of the title cephalosporin which can be converted to free base by use of ion exchange resin.

The following examples are illustrative of pharmaceutical preparations of compounds of general Formula I.

EXAMPLE 2

An illustrative composition for hard gelatin capsules is as follows:

| | |
|---|---|
| (a) 2-amino-2-difluoromethyl-3-(5-imidazolyl)propionic acid | 100 mg |
| (b) talc | 20 mg |
| (c) lactose | 500 mg |

The formulation is prepared by passing the dry powders of (a) and (b) through a fine mesh screen and mixing them well. The powder is then filled into hard gelatin capsules at a net fill of 620 mg per capsule.

EXAMPLE 3

An illustrative composition for tablets is as follows:

| | |
|---|---|
| (a) 2-amino-2-difluoromethyl-3-(5-imidazolyl)propionic acid | 200 mg |
| (b) starch | 50 mg |
| (c) lactose | 100 mg |
| (d) magnesium stearate | 5 mg |

The granulation obtained upon mixing the lactose with the compound (a) and the part of the starch and granulated with starch paste is dried, screened, and mixed with the magnesium stearate. The mixture is compressed into tablets weighing 355 mg each.

EXAMPLE 4

An illustrative composition for an aerosol solution is the following:

| | Weight percent |
|---|---|
| (a) 2-amino-2-difluoromethyl-3-[5-(2-fluoro)imidazolyl]propionic acid | 20.0 |
| (b) ethanol | 30.0 |
| (c) dichlorodifluoromethane | 50.0 |

The materials (a), (b) and (c) are packaged in 15 ml stainless steel containers equipped with a metering valve designed to meter 0.2 grams per dose, an equivalent of 40 mg of novel compound (a).

EXAMPLE 5

An illustrative composition for an injedtable suspension is the following 1 ml ampul for an intramuscular injection.

| | Weight percent |
|---|---|
| (a) 2-amino-2-fluoromethyl-3-[5-(4-methyl)imidazolyl]propionic acid | 5.0 |
| (b) polyvinylpyrrolidone (M.W. 25000) | 0.5 |
| (c) lecithin | 0.25 |
| (d) water for injection to make | 100.0 |

The materials (a)-(d) are mixed, homogenized, and filled into 1 ml ampuls which are sealed and autoclaved 20 minutes at 121° C. Each ampul contains 50 mg per ml of novel compound (a).

EXAMPLE 6

An illustrative composition for an aerosol suspension is the following:

| | Weight percent |
|---|---|
| (a) 2-amino-2-chloromethyl-3-[5-imidazolyl]propionic acid (particly size <10μ) | 20.0 |
| (b) sorbitan trioleate | 0.5 |
| (c) dichlorodifluoromethane | 39.75 |
| (d) dichlorodifluoroethane | 39.75 |

The materials (a)–(d) are packaged in 15 ml stainless steel containers equipped with a metering value designed to meter 50 mg per dose, an equivalent of 10 mg of novel compound (a).

EXAMPLE 7

Methyl 2-benzaldimine-2-difluoromethyl-3-[5-(1-trityl-)imidazolyl]propionate Methyl 2-amino-3-(1-trityl-5-imidazolyl)propionate hydrochloride (1.52 g, 34 mmoles) is treated with a saturated solution of sodium bicarbonate, and the free base is extracted with chloroform. To a solution of the oily 2-amino-3-(1-trityl-5-imidazolyl)propionate (1.31 g, 32 mmole) in 20 ml of methylene chloride is added 337 mg (0.032 M) of benzaldehyde with stirring. Stirring is continued for about 15 hours at about 25° C. after which the mixture is concentrated to an oily residue which is crystallized in ether to give the Schiff's base, methyl 2-benzaldimine-3-(1-trityl-5-imidazolyl)propionate, m.p. 132° C. To a solution of lithium diisopropylamide (3.5 mmole), prepared from diisopropylamine and n-butyllithium, in 20 ml of tetrahydrofuran cooled to −78° C. magnetically stirred and kept under nitrogen, is added slowly 1.5 g (3 mmoles) of the above-obtained Schiff's base in 18 ml of tetrahydrofuran. The reaction mixture is allowed to warm to room temperature and is then rapidly warmed to 55° C. The nitrogen inlet is replaced by a balloon filled with chlorodifluoromethane (about 300 ml). After addition of the chlorodifluoromethane the reaction mixture is kept at room temperature for about 12 hours then quenched with brine. Ether extraction gives methyl 2-benzaldimine-2-difluoromethyl-3-[5-(1-trityl)imidazolyl]propionate as a yellow and light powder.

EXAMPLE 8

2-Amino-2-difluoromethyl-3-(5-imidazolyl)propionic acid hydrochloride

A suspension of methyl 2-benzaldimine-2-difluoromethyl-3-[5-(1-trityl)imidazolyl]propionate (1.5 g, 2.7 mmole) in concentrated hydrochloric acid (15 ml) is heated at 90° C. for 15 hours. The reaction mixture is evaporated to dryness, diluted with water and carefully extracted with chloroform. The resulting oil is dissolved in dry ethanol (3 ml) and a solution of triethylamine N in ethanol is added until the pH reaches 3.5. The mixture is evaporated to dryness and washed several times with chloroform. The resulting oil is decolorized with charcoal and two crystallizations from water-ethanol yields 2-amino-2-difluoromethyl-3-(5-imidazolyl)propionic acid hydrochloride, m.p. 250° C.

EXAMPLE 9

Methyl 2-difluoromethyl-2-amino-3-(5-imidazolyl)propionate

To a solution of crude methyl 2-difluoromethyl-2-benzaldimine-3-(1-trityl-5-imidazolyl)propionate (13 g) in ether (200 ml) is added a solution of HCl 0.5 M (10 ml). The mixture is stirred at room temperature for 12 hours after which the organic phase is separated and concentrated. The residue (12 g) is taken up in chloroform (150 ml) and treated with concentrated HCl (50 ml) at room temperature for 12 hours. The aqueous phase is separated and concentrated under reduced pressure to give methyl 2-amino-2-difluoromethyl-3-(5-imidazolyl)propionate dihydrochloride.

EXAMPLE 10

2-Amino-2-difluoromethyl-3-(5-imidazolyl)propionic acid hydrochloride

A solution of methyl 2-amino-2-difluoromethyl-3-(5-imidazolyl)propionate dihydrochloride (10 g) in concentrated HCl is heated at reflux temperature for 16 hours. Concentration of the reaction mixture gives a residue which is passed on an Amberlite IR 120 H+ form resin column. Elution with a solution of HCl 2 M afforded the 2-amino-2-difluoromethyl-3-(5-imidazolyl)propionic acid hydrochloride which is recrystallized from water/ethanol.

When in the procedure of Example 7 an appropriate amount of the hydrochloride of methyl 2-amino-3-[5-(2-fluoro-1-trityl)imidazolyl]propionate, methyl 2-amino-3-[5-(4-fluoro-1-trityl)imidazolyl]propionate, methyl 2-amino-3-[5-(2-methyl-1-trityl)imidazolyl)propionate, methyl 2-amino-3-[5-(4-methyl-1-trityl)imidazolyl]propionate, methyl 2-amino-3-[5-(2,4-difluoro-1-trityl-)imidazolyl]propionate, methyl 2-amino-3-[5-(2-fluoro-4-methyl-1-trityl)imidazolyl]propionate or methyl 2-amino-3-[5-(2,4-dichloro-1-trityl)imidazolyl]propionate is substituted for methyl 2-amino-3-[5-(1-trityl-)imidazolyl]propionate the following respective compounds are obtained:

methyl 2-benzaldimine-2-difluoromethyl-3-[5-(2-fluoro-1-trityl)imidazolyl]propionate,
methyl 2-benzaldimine-2-difluoromethyl-3-[5-(4-fluoro-1-trityl)imidazolyl]propionate,
methyl 2-benzaldimine-2-difluoromethyl-3-[5-(2-methyl-1-trityl)imidazolyl]propionate,
methyl 2-benzaldimine-2-difluoromethyl-3-[5-(4-methyl-1-trityl)imidazolyl]propionate,
methyl 2-benzaldimine-2-difluoromethyl-3-[5-(2,4-difluoro-1-trityl)imidazolyl]propionate, and
methyl 2-benzaldimine-3-[5-(2-fluoro-4-methyl-1-trityl-)imidazolyl]propionate.

When an appropriate amount of the above-obtained imidazolyl propionate derivatives is substituted for methyl 2-benzaldimine-2-difluoromethyl-3-[5-(1-trityl-)imidazolyl]propionate in the procedure of Example 8 the following respective products are obtained:

2-amino-2-difluoromethyl-3-[5-(2-fluoro)imidazolyl]-propionate acid,
2-amino-2-difluoromethyl-3-[5-(4-fluoro)imidazolyl]-propionic acid,
2-amino-2-difluoromethyl-3-[5-(2-methyl)imidazolyl]-propionic acid,
2-amino-2-difluoromethyl-3-[5-(4-methyl)imidazolyl]-propionic acid, 2-amino-2-difluoromethyl-3-[5-(2,4-difluoro)imidazolyl]propionic acid, and 2-amino-2-difluoromethyl-3-[5-(2-fluoro-4-methyl-)imidazolyl]propionic acid.

When in the procedure of Example 7 an appropriate amount of dichloromethane or chlorofluoromethane is substituted for chlorodifluoromethane methyl 2-benzaldimine-2-chloromethyl-3-[5-(1-trityl)imidazolyl]propionate and methyl 2-benzaldimine-2-fluoromethyl-3-[5-(1-trityl)imidazolyl]propionate are obtained which when substituted in appropriate amounts for methyl 2-benzaldimine-2-difluoromethyl-3-[5-(1-trityl-)imidazolyl]propionate in the in the procedure of Example 8 gives respectively 2-amino-2-chloromethyl-3-(5-imidazolyl)propionic acid, m.p. 116° C. (dec.) and 2-amino-2-fluoromethyl-3-(5-imidazolyl)propionic acid.

EXAMPLE 11

N-Acetyl 2-amino-2-fluoromethyl-3-(5-imidazolyl)propionic acid

A solution of 1.87 g (0.01 mole) of 2-amino-2-fluoromethyl-3-(5-imidazolyl)propionic acid in 10 ml of 2 N sodium hydroxide solution is cooled to 5° C. To this solution, maintained at 5° C., are added simultaneously from two syringes 1.0 g (0.013 mole) of acetyl chloride and 26 ml 2 N sodium hydroxide dropwise. After 2 hours the solution is neutralized by the addition of 8 ml of 5 N hydrochloric acid followed by 0.5 ml of acetic acid. The mixture is cooled to 0° C. and the resultant N-acetyl 2-amino-2-fluoromethyl-3-(5-imidazolyl)propionic acid filtered off.

EXAMPLE 12

Methyl 2-amino-2-fluoromethyl-3-(5-imidazolyl)propionate dihydrochloride

A suspension of 4.4 g (0.024 mole) of 2-amino-2-fluoromethyl-3-(5-imidazolyl)propionic acid in 30 ml of methanol at 0° C. is saturated with dry hydrogen chloride after which the solution is heated under reflux for 12 hours. The solution is then concentrated and allowed to crystallize to afford methyl 2-amino-2-fluoromethyl-3-(5-imidazolyl)propionate, dihydrochloride (4.0 g).

EXAMPLE 13

Ethyl N-acetyl 2-amino-2-fluoromethyl-3-(5-imidazolyl)propionate monohydrochloride A solution of 2.29 g (0.01 mole) of N-acetyl 2-amino-2-fluoromethyl-3-(5-imidazolyl)propionic acid in 50 ml of ethanol is saturated with dry hydrogen chloride, then heated under reflux overnight. The solution is concentrated then cooled and the ethyl ester monohydrochloride filtered off.

EXAMPLE 14

2(2-Aminopropionamido)-2-fluoromethyl-3-(5-imidazolyl)propionic acid

A solution of 2.72 g (0.01 mole) of methyl 2-amino-2-fluoromethyl-3-(5-imidazolyl)propionate dihydrochloride and 2.1 g (0.02 mole) of triethylamine in 40 ml of dichloromethylene at 25° C. is treated with 3.4 g (0.02 mole) of benzyl chloroformate and 2.1 g of triethylamine. After 2 hours at 25° C. the solution is washed with water, dried and concentrated to afford the dicarbobenzoxy methyl ester. To this residue is added 30 ml of 40% (w/w) hydrogen bromide in dioxane and the mixture allowed to stand at 25° C. for 30 minutes. Ether (150 ml) is then added and the resultant precipitate is filtered off and added to cold bicarbonate solution then rapidly extracted into dichloromethane. The dichloromethane solution is dried and concentrated to afford methyl N-carbobenzoxy-2-amino-2-fluoromethyl-3-(5-imidazolyl)propionate (2.3 g, 0.007 mole) which is treated in 10 ml of dichloromethane with 1.6 g (0.007 mole) of N-carbobenzoxy alanine and 1.45 g (0.007 mole) of N,N'-dicyclohexylcarbodimide overnight at 25° C. The mixture is then cooled to 0° C., the precipitated dicyclohexyl urea filtered off, the organic solution washed with 1 N hydrochloric acid, bicarbonate solution, then dried and concentrated. The residue is then treated with 30 ml of 40% (w/w) hydrogen bromide in dioxane for 30 minutes at 25° C. Addition of 150 ml of ether resulted in a precipitate of the hydrobromide which was filtered off and treated overnight with 50 ml of 1 N sodium hydroxide at 25° C. The resulting solution is adjusted to neutral pH and the product isolated from an Amberlite 120 $H^+$ resin by elution with ammonia (1 M).

EXAMPLE 15

N-(2-Propionic acid)-2-amino-2-fluoromethyl-3-(5-imidazolyl)propionyl carboxamide To a solution of 1.87 g (0.01 mole) of 2-amino-2-fluoromethyl-3-(5-imidazolyl)propionic acid in 5 ml of 4 N sodium hydroxide is added 10 ml of 5% sodium carbonate and 8 ml of dioxane. The solution is cooled in an ice bath and treated with 3.9 g (0.021 mole) of benzyl chloroformate and 5 ml of 4 N sodium hydroxide, added dropwise and simultaneously from two dropping funnels. The mixture is stirred for an additional 20 minutes at 0° C., then 30 ml of ethyl acetate is added and the reaction mixture is neutralized with 6 N hydrochloric acid. The aqueous phase is extracted with ethyl acetate, the organic solutions combined, dried and concentrated to about 5 ml. Ether (15 ml) is added and the N,N'-dicarbobenzoxy-2-amino-2-fluoromethyl-3-(5-imidazolyl)propionic acid (2.9 g, 0.007 mole) filtered off. The N,N'-dicarbobenzoxy derivative is dissolved in 15 ml of methylene chloride and treated with 720 mg (0.007 mole) of alanine methyl ester in 5 ml of methylene chloride and 1.45 g (0.007 mole) of N,N'-dicyclohexylcarbodimide. The mixture is allowed to stand overnight at 25° C., then refrigerated and the precipitated dicyclohexyl urea filtered off. The filtrate is washed with N hydrochloric acid followed by 5% bicarbonate, then dried and concentrated to afford N-(2-propionic acid methyl ester)-N,N'-dicarbobenzoxy-3-amino-2-fluoromethyl-3-(5-imidazolyl)propionyl carboxamide which is dissolved in dioxane containing 15 ml of 40% (w/w) hydrogen bromide and allowed to stand at room temperature for 30 minutes. Ether (100 ml) is added and the resulting precipitate collected and suspended in 50 ml of 0.8 N NaOH and stirred overnight at 25° C. The aqueous solution is extracted with ether, neutralized, and applied to an Amberlite 120 $H^+$ resin and the product isolated by elution with ammonia (1 M).

EXAMPLE 16

N-(n-Propyl)-2-amino-2-fluoromethyl-3-(5-imidazolyl)-propionyl carboxamide, dihydrochloride N,N'-Dicarbobenzoxy-2-amino-2-fluoromethyl-3-(5-imidazolyl)propionic acid (2.9 g, 0.007 mole), prepared as described for N-(2-propionic acid)-2-amino-2-fluoromethyl-3-(5-imidazolyl)propionyl carboxamide, in 30 ml of dichloromethane is treated with 82.5 mg (0.007 mole) of thionyl chloride at 25° C. for one hour. Propylamine (820 mg, 0.014 mole) is added and the solution stirred at 25° C. for another hour. The solution is then washed with water, dried and evaporated. The residue is treated with 15 ml of a solution of dioxane containing hydrogen bromide (40% w/w) and ethanol and allowed to stand for 30 minutes at 25° C. Ether (50 ml) is then added, the resulting precipitate collected and treated with 200 ml of 1 N sodium hydroxide and 20 ml of methanol overnight at 25° C. The solvents are concentrated by evaporation and the solution extracted with dichloromethane. The organic phase is in turn extracted with 1 N HCl and the aqueous phase evaporated to afford the product.

EXAMPLE 17

2-Fluoro-4-methylhistidine

4-Methylhistidine methyl ester (free base) (10 g) is added to 35 ml of trifluoroacetic anhydride at −10° C. The mixture is stirred at 25° C. for 5 hours, then the solvent is removed under reduced pressure. Water (50 ml) is added then removed in vacuo, this procedure being repeated 3 times, followed by a similar treatment with ethanol. The residue is recrystallized from ethyl acetate-ether to afford α-N-trifluoroacetyl-4-methylhistidine methyl ester as the trifluoroacetate salt.

A solution of 1.44 g (200 mM) of $NaNO_2$ in 20 ml of water at 0° C. is added to a solution of 2.44 g (0.02 mole) of p-bromoaniline in 300 ml of 2.3 N HCl at 0° C. After 40 minutes at 0° C. the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C. the orange precipitate (6.0 g) is collected and dried, then suspended in 200 ml of ethanol containing 0.5 g of platinum oxide and subjected to catalytic hydrogen (25° C., 40 psi Paar bomb) overnight after which the catalyst is filtered off and the solvent evaporated. The residue is treated with 100 ml of water, filtered and washed with ether. The aqueous layer is evaporated and the residue recrystallized from ethanol-ether to afford α-N-trifluoroacetyl-2-amino-4-methylhistidine methyl ester.

To 100 ml of 50% aqueous $HBF_4$ at −10° C. is added α-N-trifluoroacetyl-2-amino-4-methylhistidine methyl ester (2.5 g, 8.6 mM), followed by $NaNO_2$ (0.8 g, 12 mM) in 5 ml of water. This solution is diluted with 100 ml of cold $HBF_4$ and irradiated at 0° C. with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethylacetate. The ethyl acetate solution is concentrated to afford an oily residue which is treated with 15 ml of 0.5 M sodium hydroxide for 4 hours at 25° C. After neutralization the solution is applied to an Amberlite 120 $H^+$ resin, and the product eluted with $NH_4OH$ (1 M). Evaporation of the ammonia and recrystallization from methanol gives 2-fluoro-4-methylhistidine.

EXAMPLE 18

4-Fluoro-2-methylhistidine

2-Methylhistidine methyl ester (free base) (10 g) is added to 35 ml of trifluoroacetic anhydride at −10° C. The mixture is stirred at 25° C. for 5 hours, then the solvent is removed under reduced pressure. Water (50 ml) is added and then removed in vacuo, this procedure being repeated 3 times, followed by a similar treatment with ethanol. The residue is recrystallized from ethyl acetate-ether to afford α-N-trifluoroacetyl-2-methylhistidine methyl ester as its trifluoroacetate salt.

A solution of 1.44 g (200 mM) of $NaNO_2$ in 20 ml of water at 0° C. is added to a solution of 3.44 g (0.02 mole) of p-bromoaniline in 100 ml of 2.3 N HCl at 0° C. After 40 minutes at 0° C. the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C. the orange precipitate (6.0 g) is collected and dried, then suspended in 200 ml of ethanol containing 0.5 g platinum oxide and subjected to catalytic hydrogen (25° C., 40 psi Paar bomb) overnight. The catalyst is filtered off and the solvent evaporated. The residue is treated with 100 ml of water, filtered and washed with ether. The aqueous layer is evaporated and the residue recrystallized from ethanol-ether to afford α-N-trifluoroacetyl-2-methyl-4-aminohistidine methyl ester.

To 100 ml of 50% aqueous $HBF_4$ at −10° C. is added α-N-trifluoroacetyl-2-methyl-4-aminohistidine methyl ester (2.5 g, 8.6 mM) followed by $NaNO_2$ (0.8 g, 12 mM) in 5 ml of water. This solution is diluted with cold $HBF_4$ (100 ml) and irradiated at 0° C. with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethyl acetate. The ethyl acetate solution is concentrated to afford an oily residue which is treated with 15 ml of 0.5 M sodium hydroxide for 4 hours at 25° C. After neutralization the solution is applied to an Amberlite 120 $H^+$ resin, and the product eluted with $NH_4OH$ (1 M). Evaporation of the ammonia and recrystallization from methanol gives 4-fluoro-2-methylhistidine.

EXAMPLE 19

2,4-Difluorohistidine

A solution of 1.44 g (200 mM) of $NaNO_2$ in water (20 ml) at 0° C. is added to a solution of p-bromoaniline (6.88 g, 0.04 M) in HCl (200 ml of 2.3 N) at 0° C. After 40 minutes at 0° C. the resulting solution of the diazonium salt is added to a solution of α-N-benzoylhistidine methyl ester (5.5 g, 0.1 M) in aqueous $Na_2CO_3$ (400 ml of 0.2 M). After 2 hours at 0° C. the orange precipitate (12.0 g) is collected and dried, then suspended in 400 ml of ethanol containing 0.5 g of platinum oxide and subjected to catalytic hydrogen (25° C., 40 psi Paar bomb) overnight. The catalyst is filtered off and the solvent evaporated. The residue is treated with 200 ml of water, filtered and washed with ether. The aqueous layer is evaporated and the residue recrystallized from ethanol-ether to afford α-N-benzoyl-2,4-diaminohistidine methyl ester.

To 100 ml of 50% aqueous $HBF_4$ at $-10°$ C. is added α-N-benzoyl-2,4-diamino histidine methyl ester (2.5 g), followed by $NaNO_2$ (1.6 g, 24 mM) in water (10 ml). This solution is diluted with cold $HBF_4$ (200 ml) and irradiated at 0° C. with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethyl acetate. The ethyl acetate solution is concentrated to afford an oily residue which is treated with NaOH (0.5 M, 30 ml) for 14 hours at 25° C. After neutralization the solution is applied to an Amberlite 120 H+ resin, and the product eluted with $NH_4OH$ (1 M). Evaporation of the ammonia and recrystallization from methanol gives 2,4-difluorohistidine.

The 2-alkyl or 4-alkyl and the 2,4-dialkylhistidine derivatives employed herein are prepared from 5-hydroxymethylimidazole substituted at the 2 and/or 4-positions with an appropriate lower alkyl group by the general procedure described by K. Matsumoto et al., Agr. Biol. Chem. 38 (5), 1097 (1974). The 2,4-dialkyl-5-hydroxymethylimidazoles are prepared by hydroxymethylation of the 2,4-dialkylimidazole with formaldehyde by the general procedure of M. Masui et al., Chem. Pharm. Bull. 1974, 2359. The 4-alkyl-5-hydroxymethylimidazoles are similarly prepared according to the method described by Ewins, J. Chem. Soc. 99, 2052 (1911). The 2-alkyl-5-hydroxymethylimidazoles are prepared by hydroxymethylation of 1-benzyl-2-alkylimidazoles to give 1-benzyl-2-alkyl-4-hydroxymethylimidazoles according to E. F. Godefroi et al., Rec. Trav. Chim. Pays Bas 91, 1385 (1972). The N-benzyl group is subsequently removed using $Na/NH_3$ as described, for example, by R. G. Jones, J. Am. Chem. Soc. 71, 383 (1949).

EXAMPLE 20

2,4-Dichlorohistidine

To a solution of 1.6 g (24 mM) of sodium nitrite in 16 ml of concentrated sulfuric acid at 25° C. is added 2.5 g (8.6 mM) of α-N-benzoyl-2,4-diaminohistidine in 20 ml of acetic acid at such a rate as to maintain the temperature below 35° C. This solution is then added with cooling to a solution of 10 g of cuprous chloride in 20 ml of concentrated hydrochloric acid. The combined solution is maintained at 25° C. for 10 minutes then neutralized by careful addition of cold concentrated sodium hydroxide followed by extraction with ethyl acetate. The ethyl acetate extract is concentrated to afford an oily residue which is treated with 30 ml of 0.5 M sodium hydroxide for 14 hours at 25° C. After neutralization the solution is applied to an Amberlite 120 H+ resin and eluting with 1 ammonium hydroxide and evaporation of the ammonia affords 2,4-dichlorohistidine upon recrystallization from methanol.

When in the above procedure of Example 20 an appropriate amount of cuprous bromide is substituted for cuprous chloride and hydrobromic acid is used in place of hydrochloric acid, 2,4-dibromohistidine is obtained.

The 2,4-diiodohistidine compound [D. Mackay and D. M. Shepherd, Brit. J. Pharmacol. 15, 552 (1960)] is obtained from the diazonium salt formed in situ in the procedure of Example 20, by pouring said salt into aqueous potassium iodide containing aqueous iodide.

When in the above procedure of Example 20 an appropriate amount of the α-N-benzoyl derivative of 2-amino-4-(lower)alkylhistidine methyl ester, 2-(lower)alkyl-4-aminohistidine methyl ester, wherein the lower alkyl group has from 1 to 4 carbon atoms and is straight or branched, 2-aminohistidine or 4-aminohistidine is substituted for α-N-benzyl-2,4-diaminohistidine the following compounds are obtained:

2-chloro-4-(lower)alkylhistidine,
2-(lower)alkyl-4-chlorohistidine,
2-chlorohistidine and
4-chlorohistidine, and when the procedure of Example 20 is further modified by substituting an appropriate amount of cuprous bromide for cuprous chloride and hydrobromic acid is substituted for hydrochloric acid the following compounds are obtained: 2-bromo-4(lower)alkylhistidine, 2-(lower)alkyl-4-bromohistidine, 2-bromohistidine and 4-bromohistidine.

The 2- or 4-diodohistidine derivatives and the 2-iodo-2-(lower)alkyl histidine derivatives are obtained from the 2- or 4-diazoniumhistidine derivative and the 2-diazonium-4-(lower)alkylhistidine derivatives by pouring the appropriate diazonium derivative into aqueous potassium iodide containing aqueous iodide. The 2- or 4-diazoniumhistidine derivative and the 2-diazonium-2-(lower)alkylhistidine derivatives are formed in situ when in the procedure of Example 20 the α-N-benzoyl derivative of 2- or 4-aminohistidine, 2-amino-4-(lower)alkylhistidine or 4-amino-2-(lower)alkylhistidine is substituted respectively for α-N-benzoyl-2,4-diaminohistidine.

We claim:

1. A compound of the formula

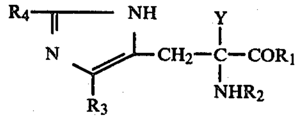

wherein Y is $F_2CH—$, $F_3C—$, or $Cl_2CH—$; each of $R_3$ and $R_4$ is hydrogen, halogen selected from fluorine, chlorine, bromine and iodine or a straight or branched lower alkyl group of from 1 to 4 carbon atoms and can be the same or different with the proviso that when both $R_3$ and $R_4$ are halogen $R_3$ and $R_4$ are the same; $R_1$ is hydroxy, a straight or branched alkoxy group of from 1 to 8 carbon atoms, $—NR_{11}R_{12}$ wherein each of $R_{11}$ and $R_{12}$ is hydrogen or a straight or branched lower alkyl group of from 1 to 4 carbon atoms or

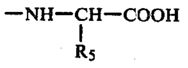

wherein $R_5$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

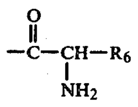

wherein $R_6$ is hydrogen, a straight or branched lower alkyl group of from 1 to 4 carbon atoms, benzyl or p-hydroxybenzyl; and pharmaceutically acceptable salts and individual optical isomers thereof.

2. A compound of claim 1 wherein $R_2$ is hydrogen or alkylcarbonyl wherein the alkyl moiety has from 1 to 4 carbon atoms and is straight or branched.

3. A compound of claim 1 wherein $R_1$ is hydroxy or a straight or branched alkoxy group of from 1 to 8 carbon atoms.

4. A compound of claim 1 wherein each of $R_3$ and $R_4$ is hydrogen, chlorine, fluorine or methyl.

5. A compound of claim 4 wherein $R_1$ is hydroxy or a straight or branched alkoxy group of from 1 to 8 carbon atoms and $R_2$ is hydrogen.

* * * * *